United States Patent [19]

Wu

[11] Patent Number: 5,639,933
[45] Date of Patent: Jun. 17, 1997

[54] ISOMERIZATION CATALYST AND USE THEREOF IN ALKANE/CYCLOALKANE ISOMERIZATION

[75] Inventor: An-hsiang Wu, Bartlesville, Okla.

[73] Assignee: Phillips Petroleum Company, Bartlesville, Okla.

[21] Appl. No.: 631,758

[22] Filed: Apr. 12, 1996

Related U.S. Application Data

[62] Division of Ser. No. 340,497, Nov. 15, 1994, Pat. No. 5,543,374.

[51] Int. Cl.$^6$ .................................................. C07C 5/22
[52] U.S. Cl. .................... 585/747; 585/741; 585/744; 585/750; 585/748; 502/334
[58] Field of Search .......................... 585/741, 744, 585/750, 748, 747; 582/334, 221

[56] References Cited

U.S. PATENT DOCUMENTS

| | | | |
|---|---|---|---|
| 2,900,425 | 8/1959 | Bloch et al. | 260/666 |
| 3,231,517 | 1/1966 | Bloch et al. | 252/442 |
| 3,755,140 | 8/1973 | Pollitzer | 208/62 |
| 3,787,313 | 1/1974 | Pollitzer | 208/60 |
| 3,963,643 | 6/1976 | Germanas et al. | 252/442 |
| 4,079,175 | 3/1978 | Tokunaga et al. | 502/128 |
| 5,004,859 | 4/1991 | Schmidt et al. | 585/741 |
| 5,474,964 | 12/1995 | Wu et al. | 502/326 |

*Primary Examiner*—Helane Myers
*Assistant Examiner*—Nadine Preisch
*Attorney, Agent, or Firm*—Charles W. Stewart

[57] ABSTRACT

A catalyst composition is prepared by a method comprising impregnating alumina with at least one platinum compound, followed by calcining, reducing treatment, and heating with gaseous aluminum chloride and gaseous titanium tetrachloride. The thus-prepared catalyst composition is employed in the isomerization of saturated $C_4$–$C_8$ hydrocarbons (alkanes and/or cycloalkanes), preferably n-butane.

18 Claims, No Drawings

ISOMERIZATION CATALYST AND USE THEREOF IN ALKANE/CYCLOALKANE ISOMERIZATION

This application is a division of application Ser. No. 08/340,497; filed Nov. 15, 1994; now U.S. Pat. No. 5,543,374.

BACKGROUND OF THE INVENTION

In one aspect, this invention relates to the preparation of a platinum-containing catalyst composition. In another aspect, this invention relates to the use of this composition as a catalyst for isomerizing saturated $C_4$–$C_8$ hydrocarbons.

Supported platinum/chlorine-containing catalyst compositions and their use in alkane isomerization reactions are well known, and are described in the patent literature, e.g., in U.S. Pat. Nos. 5,004,859 and 4,149,993. However, there are ever present incentives for the development of new, more active Pt/Cl-containing catalyst compositions and new methods of preparing them.

SUMMARY OF THE INVENTION

It is an object of this invention to provide a novel method for preparing a supported, Pt/Cl-containing catalyst composition. It is another object of this invention to provide a novel catalyst composition prepared by this preparation method. It is a further object of this invention to employ this novel catalyst composition in reactions for isomerizing saturated $C_4$–$C_8$ hydrocarbon. Other objects and advantages will become apparent from the detailed description and the appended claims.

In accordance with this invention, a method of preparing a solid platinum- and chlorine-containing composition comprises:

(a) impregnating alumina with at least one platinum compound, (b) heating the impregnated alumina obtained in step (a) at a temperature of about 300°–650° C. for a time period of at least about 5 minutes;

(c) heating the calcined material obtained in step (b) with a reducing gas; at a temperature of at least about 100° C. for a time period of at least about 5 minutes; and (d) treating (in any order) the material obtained in step (c) with gaseous aluminum chloride and gaseous titanium tetrachloride at a temperature of about 200°–800° C. for a time period of at least about 10 minutes, wherein the molar ratio of $AlCl_3$ to $TiCl_4$ is in the range of about 5:1 to about 15:1.

Also in accordance with this invention, a catalyst composition is provided which has been prepared by one of the preparation methods described above.

Further in accordance with this invention, at least one saturated feed hydrocarbon containing 4–8 carbon atoms per molecule selected from the group consisting of alkanes and cycloalkanes is isomerized to at least one corresponding saturated hydrocarbon isomer in the presence of hydrogen gas and a catalyst composition which has been prepared by the preparation method described above.

DETAILED DESCRIPTION OF THE INVENTION (A) Catalyst Preparation

Any suitable alumina material can be used in steps (a) of the preparation method of this invention. Suitable aluminas include (but are not limited to) hydrated aluminas (such as boehmite, pseudoboehmite, bayerite), alpha-alumina, beta-alumina, gamma-alumina, delta-alumina, eta-alumina and theta-alumina, preferably gamma-alumina. The alumina material generally has a surface area (determined by the BET method of Brunauer, Emmett and Teller employing $N_2$) of about 100–400 $m^2/g$, a pore volume (measured by nitrogen intrusion porosimetry) of about 0.2–1.0 $cm^3/g$, and a particle size of about 8–200 mesh. The alumina particles can be spherical, cylindrical, trilobal, or can have any other suitable shape. The presently preferred alumina particles are cylindrical extrudates. Washing of the alumina material with an acidic solution (such as an aqueous $NH_4Cl$ solution) should be avoided. Chemically bound sulfur (e.g., as sulfate) is to be substantially absent from the alumina (i.e., bound S should not be present or be present at a level of less than about 0.1 weight-% S).

Any suitable platinum compound which is water-soluble can be used in step (a) oft he preparation method of this invention. These compounds are well known and include (but are not limited to) platinum dichloride, platinum tetrachloride, hexachloroplatinic(IV) acid, ammonium hexachloroplatinate(IV), tetrammineplatinum(II) chloride, tetrammineplatinum(II) carbonate, tetrammineplatinum(II) hydroxide, dichlorodiammineplatinum(II), tetrachlordiammineplatinum(IV), platinum(II) nitrate, platinum(IV) nitrate, hexammineplatinum(II) nitrate, hexammineplatinum(IV) nitrate, diammineplatinum(IV) nitrite, diammineplatinum(II) oxalate, other complexes or coordination compounds of divalent and tetravalent platinum, and mixtures of two or more than two of these Pt compounds. Presently preferred is hexachloroplatinic acid, $H_2PtCl_6$.

The alumina material can be impregnated with at least one dissolved platinum compound in any suitable manner. Preferably, an aqueous solution of Pt compound(s) is used. Generally, the concentration of the platinum compound(s) in the aqueous impregnating solution is about 1–2 mole/l. The weight ratios of dissolved platinum compound(s) is such as to incorporate about 0.1–0.6 (preferably 0.2–0.4) weight-% Pt into the alumina material.

In step (b) of the preparation method of this invention, the Pt-impregnated alumina material obtained in step (a) is calcined at a temperature of about 300°–650° C. (preferably 450°–600° C.) for a time period of about 0.5–20 hours (preferably about 2–4 hours). This calcining step can be done in an inert atmosphere (i.e.,$N_2$, He, Ar) or in an $O_2$-containing atmosphere (e.g., air). Preferably, the Pt-impregnated alumina material is dried (e.g., at about 80°–150° C.) before step (b) carried out.

In step (c) of the preparation method of this invention, the calcined Pt-containing alumina is contacted with at least one gaseous reducing agent. Examples of such reducing gases include (but are not limited to) hydrogen and carbon monoxide. Presently preferred is $H_2$. Generally, the temperature in step (c) is about 200°–800° C. (preferably about 300°–600° C.) and the contacting time is about 0.2–10 hours (preferably about 0.5–5 hours).

In step (d), the reduced material obtained in step (c) is heated with gaseous $AlCl_3$ and gaseous $TiCl_4$. Preferably, hydrogen gas is also present during heating step (d). It is within the scope of this invention to carry out the treatment with $AlCl_3$ and $TiCl_4$ in any order or essentially simultaneously, the latter being preferred. If the chloriding treatment with $TiCl_4$ and $AlCl_3$ is carded out sequentially, it is preferred to have $H_2$ gas present in each chloriding step. Step (d) is carded out at a temperature of about 200°–800°

C. (preferably about 400°–700° C., more preferably about 550°–650° C.) for a period of time of about 0.2–20 hours (preferably about 0.5–2 hours), at a hydrogen pressure of about 100–1000 psig (preferably 300–700 psig). The molar ratio of $AlCl_3$ to $TiCl_4$ generally is in the range of about 5:1 to about 15:1, preferably in the range of about 7:1 to about 13:1, more preferably in the range of about 8:1 to about 12:1, and most preferably in the range of about 9:1 to about 11:1.

The finished catalyst composition generally contains about 0.1–0.3 (preferably about 0.15–0.2) weight-% Ti, about 0.1–1 (preferably about 0.2–0.4) weight % Pt and about 2–6 (preferably about 2.5–4) weight % Cl. The surface area, pore volume, shape and particle size of the finished catalyst composition are approximately the same as those of the alumina starting material (recited above).

(B) Isomerization Process

The catalyst of this invention is generally employed in the isomerization of saturated $C_4$–$C_8$ hydrocarbons (preferably normal alkanes). Examples of suitable feed hydrocarbons include (but are not limited to) normal butane, normal pentane, normal hexane, normal heptane, normal octane, cyclohexane, methylcyclopentane, cycloheptane and methylcycloheptane (more preferably n-butane), generally in the presence of hydrogen. These so-called hydroisomerization processes are well known and have been described in the patent literature (e.g., in U.S. Pat. Nos. 4,149,993 and 5,004,859). Generally, hydrogen is mixed with the saturated hydrocarbon feed to form a feed mixture which is contacted with the isomerization catalyst of this invention contained in an isomerization zone. The concentration of the hydrogen in the feed mixture during this contacting step shall be such as to provide a hydrogen:hydrocarbon molar ratio of at least about 0.01:1, generally about 0.01:1 to about 5:1, preferably about 0.02:1 to about 2:1. The basic isomerization reaction conditions are well known and can be varied to achieve maximum conversion of the feed hydrocarbon to the desired isomer(s) in any manner known in the art. Also, the recovery of the product isomer(s) from the reaction mixture can be carded out by any suitable separation technique, such as fractional distillation. Isomerization of normal butane (n-butane) to isobutane is the presently preferred reaction carried out with the catalyst composition of this invention.

Generally, the saturated feed hydrocarbon and $H_2$ are contacted with the catalyst (preferably present in a fixed bed) at a reaction temperature of at least about 200° F., preferably at a temperature of about 200°–500° F. In the case of n-butane isomerization, the preferred temperature is about 250°–400° F. Generally, the liquid hourly space velocity of the saturated hydrocarbon feed stream, i.e., cc of liquid feed hydrocarbon per cc of catalyst per hour, is about 0.1 to about 15. Generally, the reaction pressure is within the range of 200 psig to about 1500 psig in the isomerization zone. The gas hourly space velocity of the hydrogen feed stream is generally about 10–2,000 (preferably about 50–1000) cc $H_2$ per cc catalyst per hour (so as to give the above-recited $H_2$:hydrocarbon ratio). In order to activate the catalyst and to retard its deactivation during the isomerization reaction, about 0.001 to about 1 weight percent chloride is frequently added to the alkane feed, generally in the form of at least one chloroalkane, preferably carbon tetrachloride, chloroform, ethyl chloride or isopropyl chloride.

When the catalyst employed in the hydroisomerization process has lost its activity to the extent that the desired alkane conversion can no longer be attained at the desired reaction temperature, the catalyst can be reactivated by mining off the flow of the saturated feed hydrocarbon while maintaining the flow of the $H_2$ stream through the isomerization catalyst, generally at about the same temperature and the same gas hourly space velocity of $H_2$ as in the isomerization reaction. In the preferred reactivation mode, a reducing gas stream comprising hydrogen and, optionally, a chloriding agent is passed through the partially deactivated isomerization catalyst bed at a temperature of about 50°–400° F. (preferably about 250°–330° F.) and a GHSV (gas hourly space velocity) of about 10–2,000 cc $H_2$ per cc catalyst per hour (more preferably about 50–950 cc/cc/hour), for a time period of about 2 hours to about 10 days (more preferably about 5 hours to about 7 days). The activated catalyst is then redeployed in the hydroisomerization process of this invention.

The following examples are presented to further illustrate the present invention and are not to be construed as unduly limiting the scope of this invention.

EXAMPLE I

This example illustrates the preparation of various alumina-supported platinum catalysts. This example illustrates the preparation of various chlorided platinum-impregnated alumina materials.

Catalyst A was prepared as follows: about 15 grams of alumina (provided by Criterion Catalyst Company, Houston, Tex.; sulfur content: 0%) was impregnated (by incipient wetness) with an aqueous solution of hexachloroplatinic acid (containing 1.0 gram of $H_2PtCl_6$, 65.6 grams of water and 1.4 grams of HCl). The thus-impregnated alumina was substantially dried by means of an aspirator pump for 1–2 hours, heated in a helium gas stream at 525° C. for about 1 hour, heated an oxygen gas stream at 525° C. for several hours, cooled in a helium gas stream to 425° C., heated in a hydrogen gas stream at 425° C. for about 2 hours, and then cooled to 150° C.

Thereafter, a downflow stainless steel reactor was charged with 14.8 grams (20 cc) of the Pt-impregnated alumina and a top layer of Alundum® (inert alumina beads having a surface area of less than 1 m²/g). The reactor and its contents were heated (at a rate of 10° C. per minute) to about 595° C. while helium gas flowed through the reactor and its contents at a rate of 1.0 liter/minute. The helium gas flow was maintained at a temperature of about 595° C. for about 10 minutes. Then hydrogen gas was passed through the reactor and its contents at a rate of 0.3 liter/minute and a reactor temperature of 595° C., for a time period of 5–10 minutes. Thereafter a powder mixture of 1.75 grams. of $AlCl_3$ to $TiCl_4$ (at a molar $AlCl_3$:$TiCl_4$ ratio of about 10:1) was introduced with the dry hydrogen gas stream and was deposited on the Alundum® layer on top of the Pt/$Al_2O_3$ material in the reactor. The $H_2$ gas stream passed through the $AlCl_3$/$TiCl_4$/Alundum® layer (maintained at a temperature of 180°–280° C.) and then through the reactor containing Pt/$Al_2O_3$ material (maintained at a temperature of about 595° C.) for a time period of 1 hour during which $AlCl_3$ and $TiCl_4$ sublimed onto and interacted with the Pt/$Al_2O_3$ material. Then the $H_2$ gas stream was replaced with a helium/hydrogen gas stream containing 70 volume-% He and 30 volume-% $H_2$, and the reactor was cooled to 150° C. The finished catalyst contained 0.32 weight-% Pt and 3–4 weight-% Cl.

Catalyst B was essentially a duplicate of Catalyst A. Catalyst B contained 0.32 weight-% Pt, and 3.6 weight-% Cl.

Catalyst C was prepared essentially in accordance with the procedure for Catalyst A, except that $TiCl_4$ was introduced about 10 minutes prior to the introduction of AlCl₃. The AlCl₃:TiCl₄ molar ratio was 10:1. Catalyst C contained 0.32 weight-% Pt, and 2.7 weight-% Cl.

Catalyst D was prepared in accordance with the procedure for Catalyst A, except that the molar ratio of AlCl₃ to TiCl₄ in the mixture of the two compounds (which was placed on top of the Alundum® layer) was 20:1. Catalyst D contained 0.32 weight-% Pt, and 3.1 weight-% Cl.

Catalyst E was essentially a duplicate of Catalyst D (AlCl₃:TiCl₄ molar ratio: 20:1). It contained 0.32 weight-% Pt and 3.0 weight-% Cl.

Catalyst F was prepared essentially in accordance with the procedure for Catalyst A, except that only AlCl₃ (in lieu of AlCl₃/TiCl₄) was employed as the chloriding agent. Catalyst F contained 0.32 weight-% Pt and 3.5 weight-% Cl.

Catalyst G was prepared essentially in accordance with the procedure for Catalyst A, except that only TiCl₄ (in lieu of AlCl₃TiCl₄) was employed as the chloriding agent. Catalyst G contained 0.32 weight-% Pt and 3.7 weight-% Cl.

EXAMPLE II

This example illustrates the use of the catalyst materials described in Example I in the isomerization of n-butane.

20 cc of each catalyst was placed in a stainless steel reactor tube having an inner diameter of 1 inch and a length of 28 inches. The steel reactor tube was heated to 138° C. A stream of hydrogen gas was passed through the catalyst bed at a rate of 1.34 cubic feet per hour. The reactor pressure was about 500 psig. Liquid n-butane was introduced at a rate of 78 about cc/hour (liquid hourly space velocity:3.9 cc/cc catalyst/hour), while the flow of the hydrogen gas stream was maintained at 1.35 ft³/hour so as to provide a molar ratio of H₂ to n-butane of about 50:1. After the hydrogen/n-butane mixture had passed through the catalyst bed at the above conditions for about 10 minutes, carbon tetrachloride was injected into this feed mixture at a rate of 16 microliters per hour for a time period of up to about 24 hours. Thereafter, the CCl₄ feed rate was reduced to 6 microliters per hour, and the test was continued. The isomerization product was analyzed by means of a gas chromatograph. Pertinent catalyst preparation parameters and isomerization test results (obtained at comparable reaction conditions) are summarized in Table I.

Test data in Table I show that generally a more active isomerization catalyst was obtained when both aluminum chloride and titanium tetrachloride were used as chloriding agents, at a molar AlCl₃:TiCl₄ ratio of about 10:1.

Additional tests (not described in detail herein) indicated that washing of the Criterion alumina with a 1 molar aqueous NH₄Cl solution for about 1–6 hours prior to the catalyst preparation consistently produced catalysts of low isomerization activity. Thus, this pretreatment of alumina should be avoided. Another test (not described in detail herein) showed that the presence of about 0.5 weight-% of chemically bound sulfur in the alumina caused the resulting chlorided Pt/Al₂O₃ catalyst to have low isomerization activity. Thus, chemically bound sulfur should be substantially absent from the alumina starting material.

Reasonable variations, modifications, and adaptations for various usages and conditions can be made within the scope of the disclosure and the appended claims without departing from the scope of this invention.

That which is claimed:

1. A process for isomerizing saturated hydrocarbons which comprises contacting at least one saturated feed hydrocarbon containing 4–8 carbon atoms per molecule selected from the group consisting of alkanes and cycloalkanes at effective isomerization conditions with hydrogen gas and an effective isomerization catalyst so as to produce at least one product isomer, wherein said effective isomerization catalyst has been prepared by a method comprising the steps of (a) impregnating alumina with at least one platinum compound;

(b) heating the impregnated alumina obtained in step (a) at a temperature of about 300°–650° C. for a time period of at least 5 minutes;

(c) heating the calcined material obtained in step (b) with a reducing gas at a temperature of at least about 100° C. for a time period of at least about 5 minutes; and (d) treating the material obtained in step (c) with gaseous aluminum chloride and gaseous titanium tetrachloride at a temperature of about 400°–700° C. for a time period of at least about 10 minutes, wherein the molar ratio of AlCl₃ to TiCl₄ is in the range of about 5:1 to about 15:1.

2. A process in accordance with claim 1, wherein hydrogen gas is also present in the treating step (d).

3. A process in accordance with claim 2, wherein chemically bound sulfur is substantially absent from said alumina.

TABLE I

| Run | Catalyst | Treatment of Pt/Al₂O₃ with AlCl₃ | Treatment of Pt/Al₂O₃ with TiCl₄ | AlCl₃:TiCl₄ Mol Ratio | Wt - % Cl in Catalyst | % Isobutane in C₄ Isom Product[1] |
|---|---|---|---|---|---|---|
| 1 | A | Yes | Yes | 10:1 | N/A | 20.0 |
| 2 | B | Yes | Yes | 10:1 | 3.6 | 8.6[2] |
| 3 | C | Yes | Yes | 10:1 | 2.7 | 19.3 |
| 4 | D | Yes | Yes | 20:1 | 3.1 | 15.3 |
| 5 | E | Yes | Yes | 20:1 | 3.0 | 12 |
| 6 | F | Yes | No | — | 3.5 | 16.5 |
| 7 | G | No | Yes | — | 3.7 | 8.5 |

[1] based on isomerization product excluding H₂, produced after about 20 hours; isomerization conditions of all runs: amount of catalyst: about 20 cc (about 15 g); reaction temperature: about 138° C.; reaction pressure: about 500 psig; liquid n-butane feed rate: about 80 cc/hour; H₂ feed rate: about 1.3 ft³/hr; H₂:n-butane mol ratio: about 10:1
[2] result is considered erroneous; it is believed that a hydrogen gas dryer did not work properly and that moisture was introduced into the system.

4. A process in accordance with claim 3, wherein said alumina has not been contacted with an acidic solution prior to step (a).

5. A process in accordance with claim 2, wherein the conditions of step (a) are such as to incorporate about 0.1–1 weight-% Pt into said alumina.

6. A process in accordance with claim 2, wherein heating step (b) is carried out at a temperature of about 450°–600° C. for about 0.2–20 hours.

7. A process in accordance with claim 2, wherein step (c) is carried out with hydrogen gas at a temperature of about 300°–600° C. for a time period of about 0.2–10 hours.

8. A process in accordance with claim 2, wherein step (d) is carried out for a time period of about 0.2–20 hours, at a temperature of about 400°–700° C. and a hydrogen pressure of about 100–1,000 psig.

9. A process in accordance with claim 8, wherein step (d) is carried out at a molar ratio of $AlCl_3$ to $TiCl_4$ of about 7:1 to about 13:1.

10. A process in accordance with claim 9, wherein step (d) is carried out for a time period of about 0.5–2 hours, at a temperature of about 550°–650° C., a hydrogen pressure of about 300–700 psig and a molar ratio of $AlCl_3$ to $TiCl_4$ of about 8:1 to about 12:1.

11. A process in accordance with claim 1, wherein said effective isomerization catalyst comprises about 0.1–1 weight-% Pt, about 0.1–0.3 weight-% Ti and about 2–6 weight-% Cl.

12. A process in accordance with claim 11, wherein said effective: isomerization catalyst comprises about 0.2–0.4 weight-% Pt, about 0.15–0.2 weight-% Ti and about 2.5–4 weight-% Cl.

13. A process in accordance with claim 11, wherein said at least one saturated feed hydrocarbon is n-butane.

14. A process in accordance with claim 13, wherein said effective isomerization conditions comprise a molar ratio of hydrogen to n-butane is about 0.1:1 to about 5:1, a reaction temperature of about 200°–500° C. and a reaction pressure of about 200–1500 psig.

15. A process in accordance with claim 2, wherein said effective. isomerization catalyst comprises about 0.1–1 weight-% Pt, about 0.1–0.3 weight-% Ti and about 2–6 weight-% Cl.

16. A process in accordance with claim 15, wherein said effective isomerization catalyst comprises about 0.2–0.4 weight-% Pt, about 0.15–0.2 weight-% Ti and about 2.5–4 weight-% Cl.

17. A process in accordance with claim 15, wherein said at least one saturated feed hydrocarbon is n-butane.

18. A process in accordance with claim 17, wherein said effective isomerization conditions comprise a molar ratio of hydrogen to n-butane is about 0.1:1 to about 5:1, a reaction temperature of about 200°–500° C. and a reaction pressure of about 200–1500 psig.

* * * * *